United States Patent [19]

Bayley et al.

[11] Patent Number: 5,250,379
[45] Date of Patent: Oct. 5, 1993

[54] TONER COMPOSITIONS WITH METAL COMPLEX CHARGE ENHANCING ADDITIVES

[75] Inventors: Denise R. Bayley, Fairport; Thomas R. Pickering, Webster; Roger N. Ciccarelli, Rochester; Jacques C. Bertrand, Ontario, all of N.Y.

[73] Assignee: Xerox Corporation, Stamford, Conn.

[21] Appl. No.: 970,509

[22] Filed: Nov. 2, 1992

[51] Int. Cl.$^5$ .................. G03G 9/083; G03G 9/097
[52] U.S. Cl. .................... 430/106.6; 430/110
[58] Field of Search ..................... 430/106.6, 110

[56] References Cited

U.S. PATENT DOCUMENTS

| | | | |
|---|---|---|---|
| 4,206,064 | 6/1980 | Kiuchi et al. | 430/106 |
| 4,298,672 | 11/1981 | Lu | 430/108 |
| 4,411,974 | 10/1983 | Lu et al. | 430/106 |
| 4,845,003 | 7/1989 | Kiriu et al. | 430/110 |

FOREIGN PATENT DOCUMENTS 278570  12/1987  Japan ................... 430/110

Primary Examiner—Roland Martin
Attorney, Agent, or Firm—E. O. Palazzo

[57] ABSTRACT

A negatively charged toner composition comprised of resin particles, pigment particles, and an aluminum charge enhancing additive obtained from the reaction of an aluminum inorganic salt solution, and xanthene carboxylic acid.

21 Claims, No Drawings

TONER COMPOSITIONS WITH METAL COMPLEX CHARGE ENHANCING ADDITIVES

BACKGROUND OF THE INVENTION

The invention is generally directed to toner and developer compositions, and more specifically, the present invention is directed to developer and toner compositions containing charge enhancing additives, which impart or assist in imparting a negative charge to the toner particles and enable toners with rapid triboelectric charging characteristics. In one embodiment, there are provided in accordance with the present invention toner compositions comprised of a polymer or polymer resins, pigment particles or dye molecules, and certain metal salts, especially aluminum, charge enhancing additives. In another embodiment, the present invention is directed to toners with aluminum charge enhancing additives, which additives can be obtained from the reaction of, for example, xanthene, especially xanthene-9-carboxylic acid or coumarin, especially coumarin-3-carboxylic acid or a mixture thereof, with an aqueous solution of an aluminum inorganic salt. The aforementioned charge additives, especially bis(xanthene-9-carboxylato)hydroxy aluminum, bis(coumarin-3-carboxylato)hydroxy aluminum, or (coumarin-3-carboxylato)(xanthene-9-carboxylato)hydroxy aluminum, in embodiments of the present invention enable, for example, toners with rapid and stable triboelectric charging characteristics, and improved admix characteristics. Also, the aforementioned toner compositions usually contain a colorant component comprised of, for example, carbon black, magnetites, or mixtures thereof, color pigments or dyes, and more specifically, cyan, magenta, yellow, blue, green, red, or brown pigments, or mixtures thereof thereby providing for the development and generation of black and/or colored images. The toner and developer compositions of the present invention can be selected for electrophotographic, especially xerographic, imaging and printing processes, including color processes.

Toners with negative charge additives are known, reference for example U.S. Pat. Nos. 4,411,974 and 4,206,064, the disclosures of which are totally incorporated herein by reference. The '974 patent discloses negatively charged toner compositions comprised of resins, pigment particles, and as a charge enhancing additive ortho-halophenyl carboxylic acids. Similarly, there are disclosed in the '064 patent toner compositions with chromium, cobalt, and nickel complexes of salicylic acid as negative charge enhancing additives. In U.S. Pat. No. 4,845,003, there are illustrated negatively charged toners with certain aluminum salt charge additives. More specifically, this patent discloses as charge additives aluminum complexes comprised of two or three hydroxybenzoic acid ligands bonded to a central aluminum ion. A disadvantage of some of these charge additives is their thermal instability, that is they often break down during the thermal extrusion process of the toner manufacturing cycle. Another disadvantage is that some of these additives are colored which can render them unsuitable for use in nonblack toners. A fast rate of triboelectric charging is particularly crucial for high speed xerographic machines since, for example, these machines consume toner rapidly, and fresh toner has to be constantly added. The added uncharged toners, therefore, must charge up to their equilibrium triboelectric charge level rapidly to ensure no interruption in the xerographic imaging or printing operation. Many of these and other disadvantages are eliminated, or substantially eliminated with the metal salt charge additives of the present invention, while maintaining the rapid charging or admix, necessary for high speed xerographic machines.

Developer compositions with charge enhancing additives, which impart a positive charge to the toner particles, are also known. Thus, for example, there is described in U.S. Pat. No. 3,893,935 the use of quaternary ammonium salts as charge control agents for electrostatic toner compositions; U.S. Pat. No. 4,221,856 which discloses electrophotographic toners containing resin compatible quaternary ammonium compounds in which at least two R radicals are hydrocarbons having from 8 to about 22 carbon atoms, and each other R is a hydrogen or hydrocarbon radical with from 1 to about 8 carbon atoms, and A is an anion, for example sulfate, sulfonate, nitrate, borate, chlorate, and the halogens such as iodide, chloride and bromide, reference the Abstract of the Disclosure and column 3; a similar teaching is presented in U.S. Pat. No. 4,312,933 which is a division of U.S. Pat. No. 4,291,111; similar teachings are presented in U.S. Pat. No. 4,291,112 wherein A is an anion including, for example sulfate, sulfonate, nitrate, borate, chlorate, and the halogens; U.S. Pat. No. 4,338,390, the disclosure of which is totally incorporated herein by reference, discloses developer compositions containing as charge enhancing additives organic sulfate and sulfonates, which additives can impart a positive charge to the toner composition; U.S. Pat. No. 4,298,672, the disclosure of which is totally incorporated herein by reference, discloses positively charged toner compositions with resins and pigment particles, and as charge enhancing additives alkyl pyridinium compounds.

Illustrated in copending patent application U.S. Ser. No. 894,688 are toner compositions comprised of polymer resins, colorants comprised of color pigment particles or dye molecules, and certain metal complex charge additives derived from the reaction of a mixture of a hydroxybenzoic acid and a base with a metal ion in the presence of an excess of a hydroxyphenol. Also, in copending patent applications U.S. Ser. No. 898,610, and U.S. Ser. No. 885,589 is disclosed a negatively charged toner composition comprised of resin particles, colorants, optional surface additives, and a dihydroxyaryl sulfone charge enhancing additive, or an unsymmetrical hydroxyaryl sulfone charge enhancing additive obtained from the condensation of sulfuric acid with a molar equivalent of a phenol, followed by condensation with a second phenol, or from the condensation of an aromatic sulfonic acid with a phenol; and a negatively charged toner composition comprised of resin particles, pigment particles, and a hydrotalcite charge enhancing additive.

Although many charge enhancing additivies are known, there continues to be a need for toners with certain charge enhancing additives thus enabling many of the advantages illustrated herein. There is also a need for negative charge enhancing additives which are useful for incorporation into black and colored toner compositions and which can be utilized for developing positive electrostatic latent images. Moreover, there is a need for colored toner compositions containing charge enhancing additives which do not interfere with the color quality of the colorants present in the toners.

Another need relates to the provision of toner compositions with certain charge enhancing additives, which toners in embodiments thereof possess substantially stable triboelectric charge levels, and display acceptable rates of triboelectric charging characteristics. Furthermore, there is also a need for toner compositions with certain charge enhancing additives which possess excellent dispersibility characteristics in toner resins, and can, therefore, form stable dispersions in toner compositions thereof. There is also a need for negatively charged black and colored toner compositions that are useful for incorporation into various imaging processes, inclusive of color xerography, as illustrated in U.S. Pat. No. 4,078,929, the disclosure of which is totally incorporated herein by reference; laser printers; and additionally a need for toner compositions useful in imaging apparatuses having incorporated therein layered photoresponsive imaging members, such as the members illustrated in U.S. Pat. No. 4,265,990, the disclosure of which is totally incorporated herein by reference. Also, there is a need for negatively charged toner compositions which have desirable triboelectric charge levels of, for example, from between about −10 to about −40 microcoulombs per gram, and preferably from about −15 to about −25 microcoulombs per gram, and triboelectric charging rates of less about 120 seconds, and preferably less than 60 seconds as measured by standard charge spectrograph methods when the toners are frictionally charged against suitable carrier particles via conventional roll milling techniques. The concentrations of the charge additives that can be selected for the toner compositions generally range from about 0.05 weight percent to about 10 weight percent, depending on whether the charge additive is utilized as a surface additive or as a dispersion in the bulk of the toner. The effective concentrations of toner in the developer, that is toner and carrier particles, are for example from about 0.5 to about 10 weight percent, and preferably from about 1 to about 3 weight percent.

SUMMARY OF THE INVENTION

It is an object of the present invention to provide toner and developer compositions with negative charge enhancing additives.

In another object of the present invention there are provided negatively charged toner compositions useful for the development of electrostatic latent images including color images, and useful in hybrid scavengeless, discharge area development, inductive magnetic brush, conductive magnetic brush, single component magnetic brush, and the like.

A further object is to provide simple and cost effective processes for the preparation of metal complex charge enhancing additives.

Also, in another object of the present invention there are provided toners with rapid or improved admix charging characteristics.

These and other objects of the present invention may be accomplished in embodiments thereof by providing toner compositions comprised of a polymer or polymer resins, colorants comprised of color pigment particles or dye molecules, and certain metal complex charge additives. More specifically, the present invention in embodiments is directed to toner compositions comprised of resin particles, pigment particles, and an aluminum metal negative charge enhancing additive or mixtures thereof of the formulas

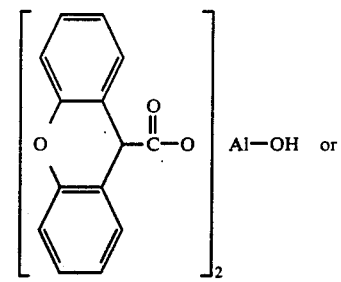

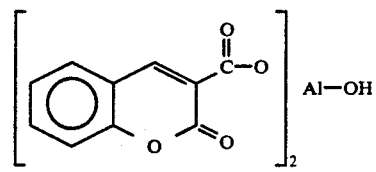

Also, in embodiments toners with aluminum metal negative charge additives of the formula are envisioned.

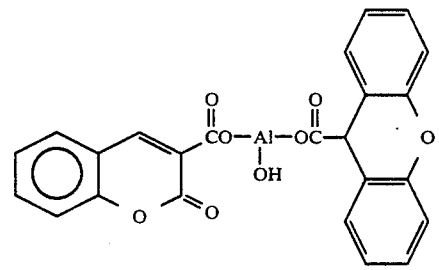

Examples of specific charge additives include bis(xanthene-9-carboxylato)hydroxy aluminum, bis(coumarin-3-carboxylato)hydroxy aluminum, (coumarin-3-carboxylato)(xanthene-9-carboxylato)hydroxy aluminum, and the like. The aforementioned coumarin xanthene can be prepared as illustrated herein, for example, by reacting coumarin and xanthene carboxylic and mixture with an aqueous aluminum inorganic salt; ratio of, for example, 1:1:1.

The aforementioned charge additives can be incorporated into the toner, may be present in effective amounts such as indicated herein like, for example from about 0.05 to about 10 weight percent on the toner surface, or may be present on toner surface additives, such as colloidal silica, titanium oxide (TiO$_2$) particles, and the like. Advantages of rapid triboelectric charging characteristics of generally less than 120 seconds, and preferably less than 60 seconds, such as about 15 to 30 seconds, in embodiments as measured by the standard charge spectrograph methods when the toners are frictionally charged against carrier particles by known conventional roll mixing methods, appropriate triboelectric charge levels, and the like can be achieved with many of the aforementioned toners of the present invention. In another embodiment of the present invention, there are provided, subsequent to known micronization and classification, toner particles with a volume average diameter of from about 5 to about 20 microns.

The aluminum charge additives of the present invention cThe charge additives can be prepared by the reaction dissolution of a xanthene, such as xanthene-9-carboxylic acid, and/or a coumarin carboxylic acid, such as coumarin-3-carboxylic acid dissolved with a known base, like sodium hydroxide, or with an aqueous aluminum inorganic salt solution such as aluminum sulfate or aluminum chloride. The ratio of the reactants is such that there are, for example, two molecules of acid for every aluminum atom. The reaction can be accomplished at temperatures ranging from about 60° C. to 95° C. The resulting product precipitate is filtered and washed with, for example, clean water and dried in, for example, a heated laboratory oven. The product can be identified by a number of know methods such as infrared analysis.

The toner compositions of the present invention can be prepared by a number of known methods such as admixing and heating polymer resins such as styrene butadiene copolymers, colorants such as color pigment particles or dye compounds, and the aforementioned metal complex charge enhancing additive, or mixtures of charge additives in a concentration, preferably ranging from about 0.5 percent to about 10 percent, in a toner extrusion device, such as the ZSK53 available from Werner Pfleiderer, and removing the resulting toner composition from the device. Subsequent to cooling, the toner composition is subjected to grinding utilizing, for example, a Sturtevant micronizer for the purpose of achieving toner particles with a volume average diameter of from about 5 to about 25 microns, and preferably from about 5 to about 12 microns, which diameters are determined by a Coulter Counter. Subsequently, the toner compositions can be classified utilizing, for example, a Donaldson Model B classifier for the purpose of removing unwanted fine toner particles.

Illustrative examples of suitable toner resins selected for the toner and developer compositions of the present invention include vinyl polymers such as styrene polymers, styrene acrylates, styrene methacrylates, styrene butadienes, acrylonitrile polymers, vinyl ether polymers, acrylate and methacrylate polymers; epoxy polymers; polyurethanes; polyamides and polyimides; polyesters; mixtures thereof; and the like. The polymer resins selected for the toner compositions of the present invention include homopolymers or copolymers of two or more monomers. Furthermore, the above mentioned polymer resins may also be crosslinked depending on the desired toner properties. Illustrative vinyl monomer components in the vinyl polymers include styrene, substituted styrenes such as methyl styrene, chlorostyrene, methyl acrylate and methacrylate, ethyl acrylate and methacrylate, propyl acrylate and methacrylate, butyl acrylate and methacrylate, pentyl acrylate and methacrylate, butadiene, vinyl chloride, acrylonitrile, acrylamide, alkyl vinyl ether and the like. Illustrative examples of the dicarboxylic acid units in the polyester resins suitable for use in the toner compositions of the present invention include phthalic acid, terephthalic acid, isophthalic acid, succinic acid, glutaric acid, adipic acid, pimelic acid, suberic acid, azelaic acid, sebacic acid, maleic acid, fumaric acid, dimethyl glutaric acid, bromoadipic acids, dichloroglutaric acids, and the like; while illustrative examples of the diol units in the polyester resins include ethanediol, propanediols, butanediols, pentanediols, pinacol, cyclopentanediols, hydrobenzoin, bis(hydroxyphenyl)alkanes, dihydroxybiphenyl, substituted dihydroxybiphenyls, and the like.

As one toner resin, there can be selected polyester resins derived from a dicarboxylic acid and a diphenol, which resins are illustrated in U.S. Pat. No. 3,590,000, the disclosure of which is totally incorporated herein by reference; polyester resins obtained from the reaction of bisphenol A and propylene oxide, followed by the reaction of the resulting product with fumaric acid, and branched polyester resins resulting from the reaction of dimethylterephthalate with 1,3-butanediol, 1,2-propanediol, and pentanetriol. Further, low melting polyesters, especially those prepared by reactive extrusion, reference U.S. Ser. No. 814,641 and U.S. Ser. No. 814,782, the disclosures of which are totally incorporated herein by reference, can be selected as toner resins. Other specific toner resins include styrene methacrylate copolymers, and styrene butadiene copolymers; PLIOLITES ®; suspension polymerized styrene butadienes, reference U.S. Pat. No. 4,558,108, the disclosure of which is totally incorporated herein by reference. Also, waxes with a molecular weight of from about 1,000 to about 7,000, such as polyethylene, polypropylene, and paraffin waxes, can be included in or on the toner compositions as fuser roll release agents.

The polymer resins are present in a sufficient, but effective amount, for example from about 30 to about 95 weight percent. Thus, when 1 percent by weight of the charge enhancing additive is present, and 10 percent by weight of colorant, such as carbon black or color pigment, is contained therein, about 89 percent by weight of resin is selected. Also, the charge enhancing additive of the present invention may be applied as a surface coating on the toner particles. When used as a coating, the charge enhancing additive of the present invention is present in an amount of from about 0.05 weight percent to about 5 weight percent, and preferably from about 0.1 weight percent to about 1.0 weight percent.

Numerous well known suitable color pigments or dyes can be selected as the colorant for the toner compositions including, for example, carbon black, like REGAL 330 ®, nigrosine dye, metal phthalocyanines, aniline blue, magnetite, or mixtures thereof. The colorant, which is preferably carbon black or other color pigments, should be present in a sufficient amount to render the toner composition with a sufficiently high color intensity. Generally, the colorants are present in effective amounts of from about 0.1 weight percent to about 20 weight percent, and preferably from about 1 to about 10 weight percent based on the total weight of the toner composition; however, lesser or greater amounts of colorant may be selected.

When the colorants are comprised of magnetites or a mixture of magnetites and color pigment particles, thereby enabling single component toners and toners for magnetic ink character recognition (MICR) applications in some instances, which magnetites are a mixture of iron oxides ($FeO.Fe_2O_3$), including those commercially available as MAPICO BLACK ®, they are present in the toner composition in an amount of from about 5 weight percent to about 70 weight percent, and preferably in an amount of from about 10 weight percent to about 50 weight percent. Mixtures of carbon black and magnetite with from about 1 to about 15 weight percent of carbon black, and preferably from about 2 to about 6 weight percent of carbon black, and magnetite, such as MAPICO BLACK ®, in an amount of, for example, from about 5 to about 70, and preferably from about 10 to about 50 weight percent can be selected for black toner compositions of the present invention.

There can also be blended with the toner compositions of the present invention external additives including flow aid additives, which additives are usually present on the surface thereof. Examples of these additives include colloidal silicas such as AEROSIL ®, metal salts and metal salts of fatty acids inclusive of zinc stearate, aluminum oxides, especially $Al_2O_3$, tin oxide, cerium oxides, titanium oxides, and mixtures thereof, which additives are generally present in an amount of from about 0.1 percent by weight to about 5 percent by weight, and preferably are present in an amount of from about 0.5 percent by weight to about 2 percent by weight. Several of the aforementioned additives are illustrated in U.S. Pat. Nos. 3,590,000 and 3,800,588, the disclosures of which are totally incorporated herein by reference.

With further respect to the present invention, colloidal silicas, such as AEROSIL ®, can be surface treated with the metal charge additives of the present invention illustrated herein in an amount of from about 1 to about 50 weight percent and preferably 10 weight percent to about 25 weight percent followed by the addition thereof to the toners in an amount of from 0.1 to 10 and preferably 0.1 to 5 weight percent.

Also, there can be included in the toner compositions of the present invention as indicated herein low molecular weight waxes, such as polypropylenes and polyethylenes, commercially available from Allied Chemical and Petrolite Corporation, EPOLENE N-15 ™ commercially available from Eastman Chemical Products, Inc., VISCOL 550-P ™, a low weight average molecular weight polypropylene available from Sanyo Kasei K. K., and similar materials. The commercially available polyethylenes selected have a molecular weight of from about 1,000 to about 1,500, while the commercially available polypropylenes utilized for the toner compositions of the present invention are believed to have a molecular weight of from about 4,000 to about 7,000. Many of the polyethylene and polypropylene compositions useful in the present invention are illustrated in British Patent No. 1,442,835, the disclosure of which is totally incorporated herein by reference. These low molecular weight wax materials are present in the toner composition of the present invention in various amounts, however, generally these waxes are present in the toner composition in an amount of from about 1 percent by weight to about 15 percent by weight, and preferably in an amount of from about 2 weight percent to about 10 weight percent.

Included within the scope of the present invention are colored toner and developer compositions comprised of toner resins, optional carrier particles, the charge enhancing additives illustrated herein, and as colorants red, blue, green, brown, magenta, cyan and/or yellow dyes or color pigments, as well as mixtures thereof. More specifically, with regard to the generation of color images utilizing a developer composition with the aluminum charge enhancing additives of the present invention, illustrative examples of magenta materials that may be selected as colorants include, for example, 2,9-dimethyl-substituted quinacridone and anthraquinone dye identified in the Color Index as Cl 60710, Cl Dispersed Red 15, diazo dye identified in the Color Index as Cl 26050, Cl Solvent Red 19, and the like. Illustrative examples of cyan materials that may be used as colorants include copper phthalocyannine, x-copper phthalocyanine pigment listed in the Color Index as Cl 74160, Cl Pigment Blue, and Anthrathrene Blue, identified in the Color Index as Cl 69810, Special Blue X-2137, and the like; while illustrative examples of yellow pigments that may be selected are diarylide yellow 3,3-dichlorobenzidene acetoacetanilides, a monoazo pigment identified in the Color Index as Cl 12700, Cl Solvent Yellow 16, a nitrophenyl amine sulfonamide identified in the Color Index as Foron Yellow SE/GLN, Cl Dispersed Yellow 33, 2,5-dimethoxy-4-sulfonanilide phenylazo-4'-chloro-2,5-dimethoxy acetoacetanilide, and Permanent Yellow FGL. The aforementioned colorants are incorporated into the toner composition in various suitable effective amounts. In embodiments, these colorants are present in the toner composition in an amount of from about 1 percent by weight to about 15 percent by weight based on the total weight of the toner.

For the formulation of developer compositions, there are mixed with the toner particles carrier components, particularly those that are capable of triboelectrically assuming an opposite polarity to that of the toner composition. Accordingly, the carrier particles of the present invention are selected to be those that would render the toner particles negatively charged while acquiring a positive charge polarity themselves via frictional charging against the toner particles of the present invention. The opposite charge polarities of the carrier and toner particles of the developer composition thus ensure the toner particles to adhere to and surround the carrier particles. Illustrative examples of carrier particles include iron powder, steel, nickel, iron, ferrites, including copper zinc ferrites, nickel zinc ferrites, and the like. Additionally, there can be selected as carrier particles nickel berry carriers as illustrated in U.S. Pat. No. 3,847,604, the disclosure of which is totally incorporated herein by reference. The selected carrier particles can be used with or without a coating, the coating generally containing terpolymers of styrene, methylmethacrylate, and a silane, such as triethoxysilane, reference U.S. Pat. Nos. 3,526,533 and 3,467,634, the disclosures of which are totally incorporated herein by reference; polymethyl methacrylates; other known coatings; and the like. The carrier particles may also include in the coating, which coating can be present in one embodiment in an amount of from about 0.1 to about 3 weight percent, conductive substances such as carbon black in an amount of from about 5 to about 30 percent by weight. Polymer coatings not in close proximity in the triboelectric series can also be selected, reference U.S. Pat. Nos. 4,937,166 and 4,935,326, the disclosures of which are totally incorporated herein by reference, including for example KYNAR ® and polymethylmethacrylate mixtures (40/60). Coating weights can vary as indicated herein; generally, however, from about 0.3 to about 2, and preferably from about 0.5 to about 1.5 weight percent coating weight is selected.

Furthermore, the diameter of the carrier particles, preferably spherical in shape, is generally from about 50 to about 1,000 microns, and preferably from between about 80 and 200 microns in volume average diameter thereby permitting them, for example, to possess sufficient density and inertia to avoid adherence to the electrostatic images during the development process. The carrier component can be mixed with the toner composition in various suitable combinations, such as about 1 to 5 parts of toner to about 100 parts to about 200 parts by weight of carrier.

The toner composition of the present invention can be prepared by a number of known methods including extrusion melt blending the toner resins, colorants, and the metal charge enhancing additive of the present invention as indicated herein, followed by mechanical attrition and classification. Other methods include those well known in the art such as spray drying, melt dispersion, extrusion processing, dispersion polymerization, and suspension polymerization. Also, as indicated herein the toner composition without the charge enhancing additive can be first prepared, followed by addition of the charge enhancing additives and other optional surface additives, or the charge enhancing additive-treated surface additives such as colloidal silicas. Further, other methods of preparation for the toner are as illustrated herein.

The toner and developer compositions of the present invention may be selected for use in electrostatographic imaging apparatuses containing therein conventional photoreceptors providing that they are capable of forming positive electrostatic latent images relative to the triboelectric charge polarity of the toners.

The toners of the present invention are usually jetted and classified subsequent to preparation to enable toner particles with a preferred volume average diameter of from about 5 to about 25 microns, and more preferably from about 5 to about 12 microns. The triboelectric charging rates for the toners of the present invention are preferably less than 120 seconds, more specifically less than 60 seconds, and from 15 to about 30 seconds in embodiments thereof as determined by the known charge spectrograph method as described hereinbefore. These toner compositions with rapid rates of triboelectric charging characteristics enable, for example, the development of images in electrophotographic imaging apparatuses, which images have substantially no background deposits thereon, even at high toner dispensing rates in some instances, for instance exceeding 20 grams per minute; and further, such toner compositions can be selected for high speed electrophotographic apparatuses, that is those exceeding 50 copies per minute.

The following Examples are being supplied to further illustrate various embodiments of the present invention, it being noted that these Examples are intended to illustrate and not limit the scope of the present invention. Comparative Examples and other Examples are also presented.

EXAMPLE I

Synthesis of Bis(xanthene-9-carboxylato)hydroxy Aluminum

To a first solution of 1.33 grams (0.033 mole) of NaOH in 75 milliliters of water were added 5 grams (0.022 mole) of xanthene-9-carboxylic acid. The resulting mixture was heated to approximately 60° C. to dissolve the acid. A second solution was prepared by dissolving 3.68 grams (0.0055 mole) of aluminum sulfate, $Al_2(SO_4)_3.18H_2O$, in 75 milliliters of water with heating to 60° C. The former solution containing the sodium salt of the acid was added rapidly and dropwise into the aluminum sulfate salt solution with stirring. A precipitate forms immediately. When the addition was completed, the reaction mixture was stirred an additional 5 to 10 minutes at 60° C. and then cooled to room temperature, about 25° C. The mixture was then filtered and the collected solid product was washed with water until the acidity of the used wash water was about 5.5 (distilled water measured 6.0). The product was dried for 16 hours in a vacuum oven at 120° F. to afford 4.21 grams (0.0085 mole, 76.9 percent of theory) of a white powder. When a sample of the product obtained was analyzed for water by Karl-Fischer titration after drying for an additional 12 hours at 100° C. in a vacuum, the sample contained 0.72 percent weight of water. The theoretical value calculated for a one mole of water for the product is 3.65 percent weight of water.

Infrared spectra of the above product indicated the presence of an aluminum carboxylate (Al—COO—) bond not present in the starting acid and a decrease of the acid peaks characteristic of the starting acid. There also appears a shoulder on the hydroxyl band (3,675 $cm^{-1}$ region) that appears to be attributed to an Al-OH band.

Elemental Analysis for $C_{28}H_{17}O_7Al$: Calculated: C, 68.2; H, 3.49; Al, 5.48. Found: C, 66.5; H, 3.83; Al, 4.62.

EXAMPLE II

Synthesis of Bis(coumarin-3-carboxylato)hydroxy Aluminum

To a solution of 1.58 grams (0.0395 mole) of NaOH in 100 milliliters of water were added 5 grams (0.026 mole) of coumarin-3-carboxylic acid and an additional 100 milliliters of water. The resulting mixture was heated to approximately 90° C. to dissolve the acid. A second solution was prepared by dissolving 4.38 grams (0.0066 mole) of aluminum sulfate $Al_2(SO_4)_3.18H_2O$ in 100 milliliters of water with heating to approximately 90° C. The former solution containing the sodium salt of the acid was added rapidly and dropwise into the latter aluminum sulfate salt solution with stirring. A precipitate forms immediately. When the addition was completed, the reaction mixture was stirred an additional 5 to 10 minutes at 90° C. and then cooled to room temperature, about 25° C. The mixture was then filtered and the collected solid product was washed with water until the acidity of the used wash water was about 5.5 (distilled water measured about 6.0). The product was dried for 16 hours in a vacuum oven at 120° F. to afford 4.74 grams (0.011 mole, 83 percent of theory) of a pale yellow powder. The Karl-Fischer analysis of the product after drying in a vacuum oven indicated that there was 3.16 percent water in the product. One mole of water in the product would equal 4.26 percent.

Infrared spectra of the above product indicated the presence of an aluminum carboxylate (Al—COO—) bond not present in the starting acid and a decrease of the acid peaks characteristic of the starting material, coumarin-3-carboxylic acid. There also appears a shoulder on the hydroxyl band (3,633 $cm^{-1}$ region) that could be attributed to an Al-OH band.

Elemental Analysis for $C_{20}H_{11}O_9Al$: Calculated: C, 56.9; H, 2.63; Al, 6.39. Found: C, 54.7; H, 2.43; Al, 4.53.

EXAMPLE III

There was prepared in an extrusion device, available as ZSK-28 from Werner Pfleiderer, a toner composition comprised of 95.5 parts of styrene/butadiene copolymer and 4.5 parts of PV FAST BLUE ™ pigment obtained from Hoechst Celanese by melt blending these components in the extruder, followed by micronization, and air classification to yield toner sized particles of 10 microns in volume average diameter as determined by a Coulter Counter. A developer was prepared by selecting 3 parts of the toner and blending it with 100 parts of Hoeganoes Anchor steel core with a particle diameter range of from about 75 to about 150 microns, available from Hoeganoes Company, as the carrier and roll milling for a period of about 30 minutes which resulted in a developer with a toner exhibiting a triboelectric charge of −8.2 microcoulombs per gram as determined by the known Faraday Cage method. A charge spectrograph analysis of the developer measured at 125 volts/centimeter resulted in a bimodal charge distribution through 60 seconds indicating that the developer without charge control additive admixed in greater than 1 minute. A second developer was prepared by selecting 3 parts of the above toner and blending it with 100 parts of carrier particles that were prepared as follows: Hoeganoes Anchor steel core with a particle diameter range of from about 75 to about 150 microns, available from Hoeganoes Company, was solution coated with 1 part by weight of a coating comprising 20 parts by weight of VULCAN ™ carbon black, available from Cabot Corporation, homogeneously dispersed in 80 parts by weight of polymethylmethacrylate, which coating was solution coated from toluene. Roll milling for a period of about 30 minutes resulted in a developer with a toner exhibiting a triboelectric charge of −7.0 microcoulombs per gram. A charge spectrograph analysis of the developer measured at 125 volts/centimeter resulted in a bimodal charge distribution through 60 seconds indicating that the developer without charge control additive admixed in greater than 1 minute.

EXAMPLE IV

A toner was prepared as follows: 94.5 parts of styrene/butadiene copolymer, 4.5 parts of PV FAST BLUE ™ pigment from Hoechst Celanese and 1 part of the hydroxy aluminum compound of Example I were melt blended in an extruder followed by micronization and air classification to yield toner sized particles of 10 microns in volume average diameter. A developer was prepared by blending 3 parts of the toner with the coated carrier of Example III and roll milling for a period of about 30 minutes which resulted in a developer with a toner exhibiting a triboelectric charge of −10.19 microcoulombs per gram. A charge spectrograph analysis of the developer measured at 125 volts/centimeter resulted in a 15 to 30 second admix, evidencing an improvement in admix performance over the same tomer with no charge control additive.

EXAMPLE V

A toner was prepared as in Example IV except 3 parts of the hydroxy aluminum compound prepared in Example I was used. A developer was prepared by repeating the process of Example IV. The resulting developer exhibited a triboelectric charge of −12.99 microcoulombs per gram. A charge spectrograph analysis of the developer measured at 125 volts/centimeter resulted in a 15 to 30 second admix.

EXAMPLE VI

A toner was prepared by repeating the process of Example IV except that 1 part of the hydroxy aluminum compound as prepared in Example II was selected as the charge additive. A developer with this toner was prepared by repeating the process of Example IV except the bare steel carrier as in Example III was used instead of the coated carrier, resulting in a triboelectric charge of −15.71 microcoulombs per gram. A charge spectrograph analysis of the developer measured at 125 volts/centimeter resulted in a 15 to 30 second admix.

Toners with a charge additive like (coumarin-3-carboxylato) (xanthene-9-carboxylato) hydroxy aluminum, and developers thereof were prepared by substantially repeating the processes of the above Examples and substantially similar results were obtained.

Other modifications of the present invention may occur to those skilled in the art subsequent to a review of the present application. The aforementioned modifications, including equivalents thereof, are intended to be included within the scope of the present invention.

What is claimed is:

1. A negatively charged toner composition comprised of resin particles, pigment particles, and an aluminum charge enhancing additive obtained from the reaction of an aluminum inorganic salt solution, and xanthene carboxylic acid.

2. A negatively charged toner composition comprised of resin, pigment, and an aluminum charge enhancing additive of the following formula

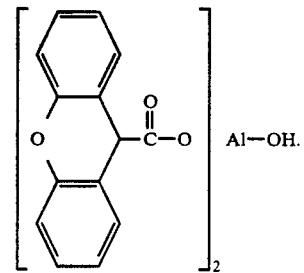

3. A toner composition in accordance with claim 2 wherein the charge additive is present in an amount of from about 0.05 to about 5 weight percent.

4. A toner composition in accordance with claim 2 wherein the charge additive is present in an amount of from about 0.1 to about 3 weight percent.

5. A toner composition in accordance with claim 2 wherein the charge additive is incorporated into the toner.

6. A toner composition in accordance with claim 2 wherein the charge additive is present on the surface of the toner composition.

7. A toner composition in accordance with claim 6 wherein the charge additive is contained on colloidal silica particles, or on titanium dioxide particles.

8. A toner composition in accordance with claim 2 wherein the toner's rate of charging is from about 15 seconds to about 60 seconds by frictional charging against suitable carrier particles via roll milling.

9. A toner composition in accordance with claim 2 with a negative triboelectric charge of from between about −10 to about −40 microcoulombs per gram.

10. A toner composition in accordance with claim 2 wherein the resin is relected from the groups consisting of styrene polymers, acrylic polymers, methacrylic polymers, polyesters, or mixtures thereof.

11. A toner composition in accordance with claim 2 wherein the resin is selected from the group consisting of styrene acrylates, styrene methacrylates, or styrene butadienes.

12. A toner composition in accordance with claim 2 containing a wax component which has a weight average molecular weight of from about 1,000 to about 7,000.

13. A toner composition in accordance with claim 12 wherein the wax component is selected from the group consisting of polyethylene and polypropylene.

14. A toner composition in accordance with claim 2 wherein the toner further includes surface additives of metal salts of a fatty acid, colloidal silicas, metal oxides, or mixtures thereof.

15. A toner composition in accordance with claim 1 wherein the pigment particles are carbon black, magnetites, or mixtures thereof, cyan, magenta, yellow, red, blue, green, or brown pigments, and mixtures thereof.

16. A toner composition in accordance with claim 2 wherein the pigment is carbon black, magnetites, or mixtures thereof, cyan, magenta, yellow, red, blue, green, brown pigments or dyes, and mixtures thereof.

17. A toner composition in accordance with claim 1 wherein the charge additive is bis(xanthene-9-carboxylato) hydroxy aluminum.

18. A developer composition comprised of the toner composition of claim 1 and carrier particles.

19. A developer composition comprised of the toner composition of claim 2 and carrier particles.

20. A developer composition in accordance with claim 19 wherein the carrier particles are selected from the group consisting of ferrites, steel, or an iron powder with a coating thereover comprised of a polymer or mixture of polymers.

21. A toner composition in accordance with claim 4 wherein the metal oxides are selected from the groups consisting of aluminum oxides, titanium oxides, or mixtures thereof.

* * * * *